United States Patent

Mays et al.

[11] Patent Number: 5,848,898
[45] Date of Patent: Dec. 15, 1998

[54] DENTURE THAT FACILITATES CHEWING ACTION

[76] Inventors: Ralph C. Mays, 5436 S. Mingo Rd., Tulsa, Okla. 74146; Gary A. Radford, 3746 E. 64th Pl., Tulsa, Okla. 74136; Michael H. Fink, 15848 E. Ruskin La., Fountain Hills, Ariz. 85268

[21] Appl. No.: 899,215

[22] Filed: Jul. 23, 1997

[51] Int. Cl.⁶ ............................................. A61C 13/08
[52] U.S. Cl. ............................................. 433/198
[58] Field of Search ................................. 433/197, 198

[56] References Cited

U.S. PATENT DOCUMENTS

| | | | |
|---|---|---|---|
| 2,168,530 | 8/1939 | Kyprie | 433/198 |
| 2,300,577 | 11/1942 | La Due et al. | 433/198 |
| 2,397,407 | 3/1946 | Butler | 433/198 |
| 2,593,815 | 4/1952 | Vivaver | 433/198 |
| 4,525,146 | 6/1985 | Lewis et al. | 433/198 |
| 5,380,203 | 1/1995 | Moodely | 433/197 |

FOREIGN PATENT DOCUMENTS

| | | | |
|---|---|---|---|
| 634766 | 3/1950 | United Kingdom | 433/198 |

*Primary Examiner*—Cary E. O'Connor
*Attorney, Agent, or Firm*—Head Johnson & Kachigian

[57] ABSTRACT

An improved denture having a gum simulating base with a curved recess therein configured to fit the alveolar ridge of a user with simulated teeth supported by the base, some of the teeth having exposed chewing surfaces and an elongated chew enhancing bar of thin metal positioned within adjacent teeth having chewing surfaces, the bar having a generally rectangular cross-sectional configuration with opposed first and second longitudinal edges, the bar first longitudinal edge being exposed at the chewing surfaces of at least three adjacent teeth.

4 Claims, 1 Drawing Sheet

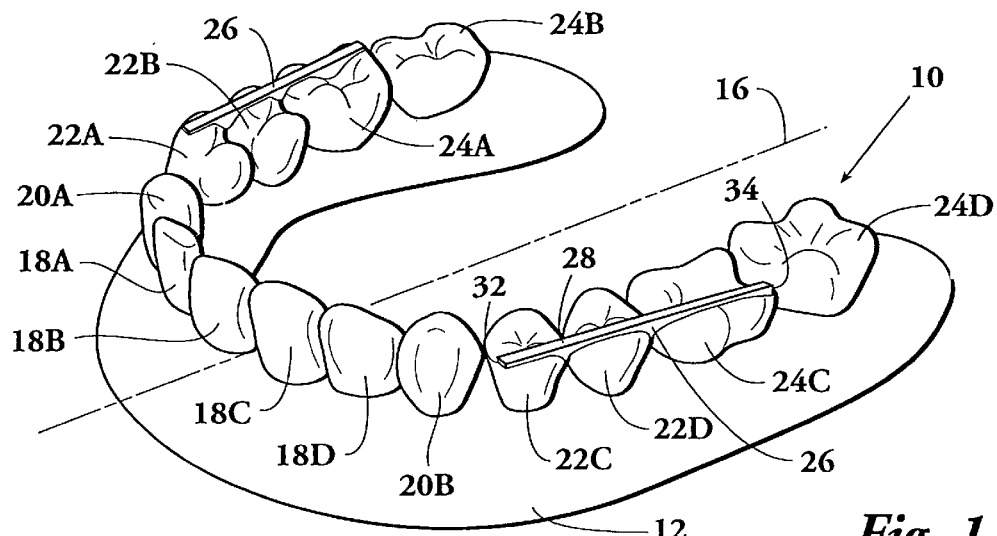
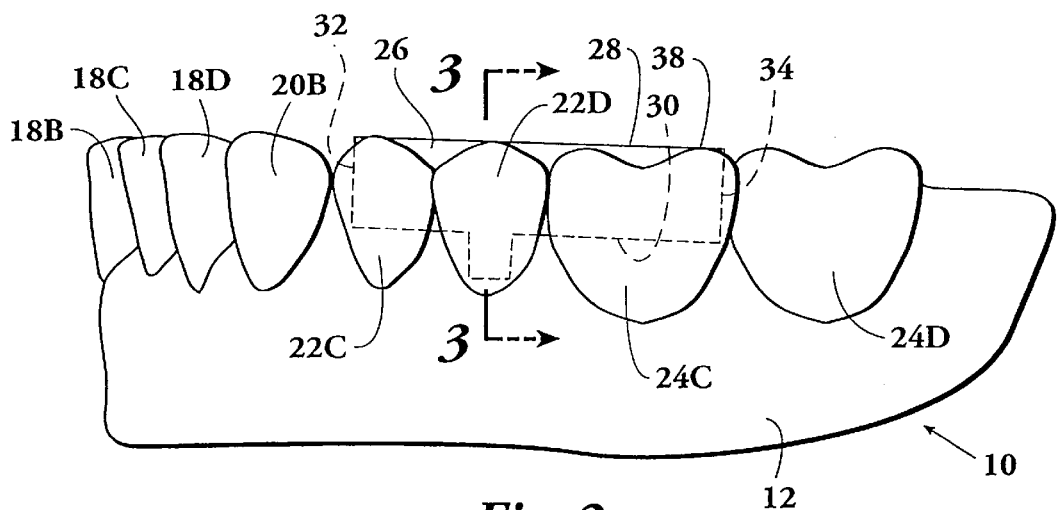
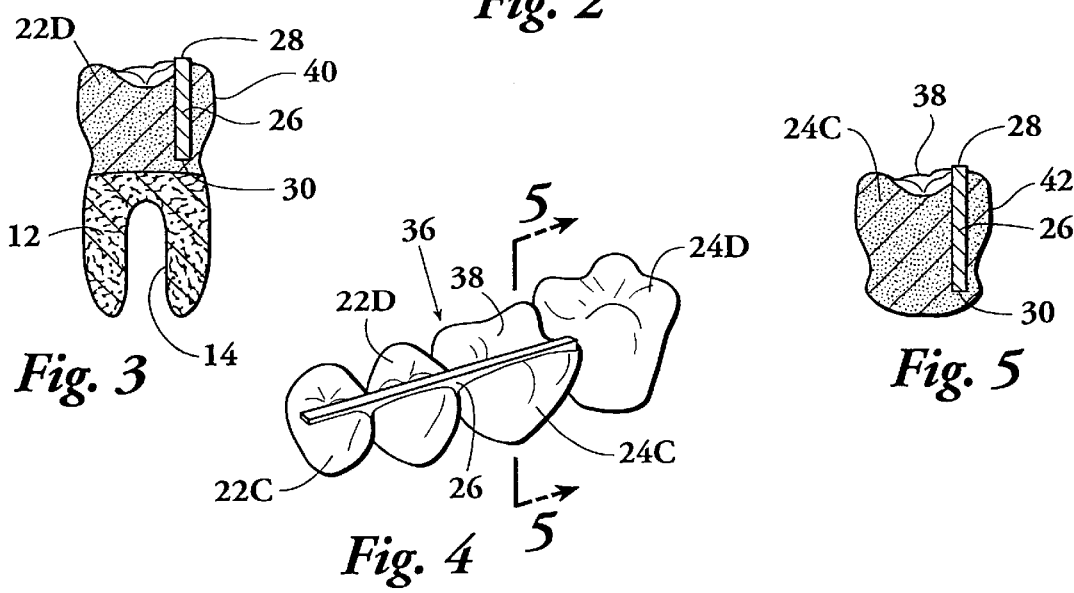

DENTURE THAT FACILITATES CHEWING ACTION

BACKGROUND OF THE INVENTION

Field of the Invention

When a person loses a portion of or all of his or her natural teeth in the upper or lower jaws a customary procedure is to fit the person with a denture. Dentures are typically formed of high grade plastics and castible ceramics and normally consist of a gum simulating base portion with simulated teeth extending therefrom. The gum simulating base portion has a recess therein configured to closely adhere to the exterior surface of the alveolar ridge of the user.

Well made dentures provide the appearance and utility of natural teeth and substantially enhance the quality of life of the user.

When full dentures are employed, that is, wherein there are no natural remaining teeth in either the upper or lower jaw of the user, the dentures are usually completely removable, that is, they have no anchoring mechanism. In recent years dental posts have been employed in some instances for anchoring dentures, but many users do not have anchoring posts or any remaining natural teeth to which dentures can be supported. Therefore full dentures are subject to movement in the mouth of the user. While such full dentures that have no anchoring mechanism function completely successfully for the user in talking, drinking or normal use, a problem exists when chewing food, particularly food that must be fully masticated since grinding of the teeth together to achieve mastication imposes significant lateral forces on the teeth.

The present invention provides improved dentures that have improved means of enhancing the ability of the user of the dentures to chew food. Particularly, the improved dentures of this invention include means to more effectively chew food to thereby reduce the lateral forces that are applied during chewing action and to thus improve the performance of dentures and the usefulness and comfort to the user.

SUMMARY OF THE INVENTION

An improved denture is provided that includes a gum simulating base having a curved recess therein configured to fit the alveolar ridge of the user. The denture may be, as an example, a complete upper denture, a complete lower denture, or an upper or lower denture that includes at least substantially all of the upper or lower teeth used for chewing.

Simulated teeth are supported by the base, at least some of the teeth in the denture have a exposed chewing surface. Chewing is accomplished by a use of opposed upper and lower premolars and molars. The teeth normally occurring in the upper or lower jaw of a human includes four incisors (the front portion of the teeth), two opposed canines adjacent the incisors, four opposed premolars, two on either side of the opposed canines, and at least two molars, rearwardly of the adjacent premolars. Most humans naturally include three molars on each side of both the upper and lower teeth, this third molar on each side being referred to as a "wisdom tooth". In many people wisdom teeth do not appear or if they do appear a modern dental practice typically includes extraction of wisdom teeth to allow the remaining teeth more room in the mouth since the wisdom teeth are not necessary for effective chewing. Therefore, a typical full denture has four incisors, two canines, four premolars and four molars and is symmetrically divided in first and second halves, each half including two incisors, one canine, two premolars and two molars in that order extending from the front to the rearward portion of the denture.

To enhance chewing this invention provides, in a denture, an elongated bar of thin metal that is positioned within at least three adjacent molars and premolars. In the preferred arrangement the chew enhancing bar is positioned within one molar and two adjacent premolars.

The elongated chew enhancing bar is of generally rectangular cross-sectional configuration and has opposed first and second longitudinal edges and opposed ends. The bar is positioned within adjacent premolars and molars with the first longitudinal edge of the bar being exposed at the teeth chewing surfaces.

In a preferred embodiment the denture of this invention has the chew enhancement bar positioned adjacent the outer edge of the teeth in which it is embedded, that is, particularly in the outer edge of at least three adjacent premolars and molars. In the most preferred arrangement the chew enhancement bar is embedded adjacent the outer surface of two premolars and a molar with one longitudinal edge of the bar exposed at the chewing surfaces of the premolars and the molar.

The chew enhancement bar is preferably formed of stainless steel or other high strength corrosion resistant metal.

In order to conveniently employ the invention in forming a denture by a dental technician, a subassembly may be used. The subassembly includes an integral casting simulating the outer portion of at least three adjacent teeth, each tooth having a chewing surface. In the preferred arrangement the subassembly is an integral casting including two premolars and one or two molars. The premolars and at least one molar has embedded therein an elongated chew enhancement bar of thin metal. The bar, as previously stated, has a generally rectangular cross-sectional configuration with opposed first and second longitudinal edges. The bar is embedded in the simulated portions of teeth with the first longitudinal edge of the bar exposed at the teeth chewing surfaces. In the most preferred arrangement the bar is embedded adjacent the outer edge of the teeth.

A better understanding of the invention will be obtained from the following description and claims, taken in conjunction with the attached drawings.

BRIEF DESCRIPTION OF THE DRAWINGS

FIG. 1 is an isometric view of a replaceable denture, the type used to fit the alveolar ridge of the lower jaw of a user and showing the employment of two chew enhancement bars.

FIG. 2 is an elevational view of one side of the denture of FIG. 1 showing the position of the chew enhancement bar.

FIG. 3 is a cross-sectional view taken along the line 3—3 of FIG. 2.

FIG. 4 is an isometric view of a subassembly of cast stimulated teeth that can be employed by a dental technician in making a denture. The subassembly includes a chew enhancement bar of this invention.

FIG. 5 is a cross-sectional view of the subassembly as taken along the line 5—5 of FIG. 4.

DETAILED DESCRIPTION OF THE PREFERRED EMBODIMENTS

Referring first to FIG. 1, an isometric view of a typical denture is indicated generally by the numeral 10, the denture 10 being an example of the type employed by a person having lost all of his or her teeth from the lower jaw.

Denture 10 is an example of the application of the invention and the invention is equally applicable to a denture that fits the upper jaw of an individual. However, the general appearance of an upper denture is different from the lower denture in that typically the upper denture is configured to conform to the internal upper surface of the mouth of the user and therefore is not of the typical U-shape configuration of the lower denture as shown in FIG. 1.

Denture 10 includes a gum simulating base 12 that has, as seen in FIG. 3, a recess 14 therein that is configured to fit the alveolar ridge of the lower jaw of the user. The alveolar ridge is the gum covered bone structure that remains after all natural teeth have been extracted. Base 12, including particularly recess 14, is formed in response to an impression made of the user's mouth and particularly the alveolar ridge since it is imperative that the denture carefully and comfortably fit the configuration of the alveolar ridge.

Formed permanently with base 12 are simulated teeth. In the embodiment of FIG. 1 a full denture is illustrated consisting of fourteen teeth that are divided symmetrically about a center line 16. A lower set of human teeth usually includes four incisors 18A through 18D, two on either side of center line 16. The function of incisors 18A–18D are primarily for biting. Adjacent the incisors are opposed canine teeth 20A and 20B, that is, one on either side of center line 16. Adjacent the incisors are two premolars 22A and 22B on one side of center line 16 and 22C and 22D on the other side of the center line. Rearwardly of the premolars are molars 24A and 24B on one side of center line 16 and 24C and 24D on the other side of the center line. Many humans produce, an addition to the four molars illustrated, an additional molar on either side of the center line that is referred to as a "wisdom tooth". For some people wisdom teeth do not appear or if they do appear, in many instances they are extracted. But, in any event, when dentures are prepared normally only two molars on each side of the center line are employed to produce fourteen simulated teeth as illustrated for either the upper or lower denture.

When a denture is placed in the mouth of the user the basic function of the incisors 18A through 18D is to bite, the canines 20A and 20B to tear and the premolars 22A through 22D and molars 24A through 24D to chew. The lower denture set as shown in FIG. 1 mashes against upper dentures, either natural teeth or a denture that has corresponding upper teeth. The natural action of chewing occurs when the user presses food between upper and lower premolars and molars and with sideways action squashes and grinds the food to break it up for swallowing and for digestion. With natural teeth, which are securely anchored in the upper and lower jaw bone, a person may apply substantial force of the upper and lower teeth against each other for the chewing action, that is, the upper and lower premolars and molars can be tightly forced against each other and the lower jaw moves side to side with respect to the upper with substantial force. However, when either the upper or -lower teeth of an individual are replaced by a removable denture, the amount of force that can be applied, particularly during the side to side action of chewing, is more restricted. To improve the chewing action of dentures, an elongated chew enhancing bar 26 is embedded in a selected number of the premolars and molars. As indicated in FIG. 1, a chew enhancing bar 26 is embedded in premolars 22A and 22B and molar 24A in the right hand side of denture 10 and in premolars 22C and 22D and molar 24C in the left hand side of the denture of FIG. 1. Chew enhancing bar 26 can extend to be partially encompassed within distal molars 24B and 24D if desired however, it has been learned that placement of chew enhancing bar 26 in the two premolars and the proximal molar on each side of a denture, as illustrated in FIG. 1, provides substantially enhanced chewing action.

The chew enhancing bar 26, as seen in cross-section in FIG. 3, is an elongated bar of metal having upper longitudinal edge 28 and opposed lower longitudinal edge 30. FIG. 1 shows the bar ends 32 and 34. Bar 26 is generally rectangular in cross-section and relatively thin.

Bar 26 may typically be about 0.030" in thickness, about 0.125" in height, and 0.750" in length. These dimensions are by example only and are the dimensions of a bar that has proven to function satisfactorily, although obviously the dimensions of the bar can change while maintaining the principle of the invention.

FIG. 4 is an isometric view of a subassembly of a casting forming the top and outer portions of four teeth. The casting including a chew enhancing bar 26. The subassembly, indicated by numeral 36, can be used by a dental technician in fabricating an upper or a lower denture. The subassembly shows the four teeth, that is two premolars and two molars in substantially a straight line with bar 26. This type of subassembly can be used in a great majority of dentures since the distal teeth are typically substantially in alignment whereas the forward teeth, beginning with the canines, provide the curved front portion of dentures. Subassemblies of teeth are typically manufactured and sold separately for use by a dental technician. The subassembly 36 having bar 26 cast in the teeth provides an easy method for a dental technician to employ the principals of this invention.

FIG. 5 is a cross-sectional view of the subassembly of FIG. 4 showing the mounting of bar 26 within the teeth.

Each of the teeth have an outside edge, such as outside edge 40 of premolar 22D as seen in FIG. 3 and outside edge 42 of molar 24C as seen in FIG. 5. Bar 26 is preferably positioned within the teeth adjacent their outside edges, such as outside edges 38 and 40. This has been found to enhance the chewing action and the bar functions to strengthen the outer portions of the teeth to reduce the possibility of portions of the simulated teeth breaking off during chewing action.

Bar 26 is preferably made of a metal, such as stainless steel, that has good wear characteristics, is highly resistant to deterioration in the mouth and is non-toxic.

Each of the premolars and molars have a chewing surface. As an example, molar 24C has a chewing surface 28. Bar 26 is preferably mound so that longitudinal edge 28 is exposed at the chewing surfaces of the teeth within which the bar is positioned.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An improved denture comprising:

a gum simulating base having a curved recess therein configured to fit the alveolar ridge of a user;

simulated teeth supported by said base, the teeth being arranged in a pattern corresponding to the typical arrangement of naturally occurring teeth in which the denture is substantially symmetrical about a plane perpendicular to a plane of said base dividing said teeth into opposed left and right hand portions, the simulated teeth of each portion including two premolars and at least first and a second molars, the first of the molars being adjacent the two premolars, the two premolars and the first, adjacent molar having exposed chewing surfaces; and an elongated chew enhancing bar of thin metal, the bar having a generally rectangular cross-sectional configuration with opposed first and second longitudinal edges and opposed ends, the bar being positioned within only said two premolars and said first, adjacent molar with the first longitudinal edge of the bar being exposed at the said chewing surfaces and said second molar being free of said bar.

2. An improved denture according to claim 1 wherein said two premolars and said first adjacent molar chewing surfaces have outside edges and wherein said chew enhancing bar is positioned adjacent the outside edges of said two premolars and said first adjacent molar.

3. A subassembly for use by a dental technician to make a denture for a patient comprising:

an integral casting simulating only two premolars and a single adjacent molar, each tooth having a chewing surface, and having embedded therein an elongated chew enhancing bar of thin metal, the bar having a generally rectangular cross-sectional configuration with opposed first and second longitudinal edges and opposed ends, the bar being positioned within only said single two premolars and said adjacent molar with said first longitudinal edge of the bar being exposed at the teeth chewing surfaces.

4. A subassembly according to claim 3 wherein said at least two premolars and said adjacent molar have outer edges and wherein said chew enhancing bar is positioned adjacent said outer edges.

* * * * *